US011141355B2

(12) United States Patent
MacDonald et al.

(10) Patent No.: US 11,141,355 B2
(45) Date of Patent: Oct. 12, 2021

(54) CARIES-RESISTANT COMPOSITE RESIN

(71) Applicant: Den-Mat Holdings, LLC, Lompoc, CA (US)

(72) Inventors: Jeff MacDonald, Lompoc, CA (US); Alvin Kobashigawa, Mission Viejo, CA (US)

(73) Assignee: Den-Mat Holdings, LLC, Lompoc, CA (US)

(*) Notice: Subject to any disclaimer, the term of this patent is extended or adjusted under 35 U.S.C. 154(b) by 0 days.

(21) Appl. No.: 16/570,984

(22) Filed: Sep. 13, 2019

(65) Prior Publication Data
US 2020/0009020 A1 Jan. 9, 2020

Related U.S. Application Data

(63) Continuation-in-part of application No. 15/613,164, filed on Jun. 3, 2017, now abandoned.

(60) Provisional application No. 62/345,578, filed on Jun. 3, 2016, provisional application No. 62/434,175, filed on Dec. 14, 2016.

(51) Int. Cl.
A61C 5/00 (2017.01)
A61K 6/00 (2020.01)
A61K 6/77 (2020.01)
A61K 6/54 (2020.01)
A61K 6/62 (2020.01)
A61K 6/802 (2020.01)
A61K 6/887 (2020.01)

(52) U.S. Cl.
CPC .............. A61K 6/77 (2020.01); A61K 6/54 (2020.01); A61K 6/62 (2020.01); A61K 6/802 (2020.01); A61K 6/887 (2020.01)

(58) Field of Classification Search
CPC .. C04B 14/42; A61K 6/30; A61K 6/35; A61K 6/77; A61K 6/889; A61K 6/17; A61K 6/54; A61K 6/836; A61K 6/50; A61K 6/833; A61K 6/20; A61Q 11/00
See application file for complete search history.

(56) References Cited

U.S. PATENT DOCUMENTS

| 5,861,445 | A | 1/1999 | Xu et al. | |
|---|---|---|---|---|
| 6,300,390 | B1 | 10/2001 | Angeletakis | |
| 6,353,041 | B1 * | 3/2002 | Qian | A61K 6/54 523/116 |
| 6,386,865 | B1 * | 5/2002 | Suh | A61C 13/0003 264/16 |
| 6,593,395 | B2 | 7/2003 | Angeletakis et al. | |
| 6,890,968 | B2 | 5/2005 | Angeletakis et al. | |
| 2003/0175669 | A1 | 9/2003 | Yin et al. | |
| 2003/0194682 | A1 * | 10/2003 | Jensen | A61K 6/893 433/224 |
| 2009/0036565 | A1 * | 2/2009 | Utterodt | A61K 6/77 523/116 |
| 2010/0210753 | A1 * | 8/2010 | Ritter | C03C 12/00 523/117 |
| 2011/0250558 | A1 * | 10/2011 | Maletz | A61K 6/887 433/89 |

FOREIGN PATENT DOCUMENTS

| WO | WO-0002525 A1 * | 1/2000 | A61K 6/887 |
|---|---|---|---|
| WO | WO-2015148318 A1 * | 10/2015 | C09K 5/14 |

* cited by examiner

Primary Examiner — Tracy Liu
(74) Attorney, Agent, or Firm — The Law Office of Fred Tong; Frederick W. Tong

(57) ABSTRACT

A direct filling composite resin restorative featuring a CTE that is similar to dentin and an antimicrobial is disclosed. The exemplary anti-microbial compound is zinc oxide. The CTE of the direct filling composite resin restorative is in the range of 12-15 ppm/° C. The low CTE is achieved by high filler loading of a trimodal distribution of low CTE filler. By maintaining a CTE substantially similar to that of dentin, the "Marginal Percolation" phenomenon is minimized, which decreases the incidence of secondary caries.

19 Claims, No Drawings

CARIES-RESISTANT COMPOSITE RESIN

CROSS-REFERENCE TO RELATED APPLICATIONS

This application is a Continuation-in-Part of U.S. non-provisional patent application Ser. No. 15/613,164, filed Jun. 3, 2017, which claims the benefit of U.S. provisional patent application Ser. No. 62/345,578, filed Jun. 3, 2016, entitled "Caries-Resistant Composite Resin" and Ser. No. 62/434,175, filed Dec. 14, 2016 entitled "Caries-Resistant Composite Resin", the contents of which are incorporated herein by reference.

FIELD OF THE INVENTION

The present invention relates to improvements in tooth treatment compositions. In particular, this invention relates to direct filling dental composite resin restoratives with increased resistance to secondary caries formation.

BACKGROUND OF THE INVENTION

Direct fill composite resins (also referred to as direct fill restoratives) were first introduced to dentistry in the late fifties. They contained particulate fillers and had improved physical properties over unfilled resins. The polymerization shrinkage was lower and long-term clinical performance looked promising, especially with respect to wear resistance and reduced secondary caries. In the early sixties, bis-GMA was introduced as a resin matrix, which further improved the properties of composite resins. However, high wear rates were observed clinically in posterior restorations. Because of this, early direct fill composite resin research has been devoted to improving wear resistance. In time, the wear resistance improved and in the early eighties, the use of direct fill composite resins in posterior restorations became acceptable. Today, the wear resistance and clinical performance of direct fill composite resins typically exceeds ten (10) years and direct fill composite resins are now the restoration of choice by dentists to directly fill cavity preparations.

Despite the improvements, development of secondary caries in the fillings continues to be a problem, which has continued throughout its existence. As an illustration, modern composite resins still have an average clinical life of about 8-10 years. in clinical studies. However, the real-world service life goes down to about 5.7 years. The shorter service life is attributed to the development of secondary caries along with bulk fractures in the field. Secondary caries are caries that occur in a tooth after a restorative has been placed. When this occurs, the restoration must be replaced.

In order to reduce secondary caries in direct fill composite resins, several research strategies were employed in the past to prevent formation of gaps between the tooth and restorative. One strategy was to reduce the polymerization shrinkage during curing of the restoration. Shrinkage stress between the tooth and restoration was thought to be a major reason for gap formation between the tooth and restoration, resulting in caries formation within the gaps. This is still a major focus in research today. To reduce shrinkage, direct fill composite resins with particulate fillers were developed, which lowered the shrinkage by about 50% (by reducing the total resin content). This was a main reason for optimism in improving clinical performance. Shrinkage has also been reduced in the resin matrix itself, for example with monomers that expand on polymerization. Together, volume shrinkage has been reduced from about 3% to less than 1%. Despite years of development, there are no clinical studies that show reduction in the secondary caries rate.

A corollary to preventing gap formation by reducing polymerization stress is to reduce development of stress by matching the Coefficient of Thermal Expansion (CTE) of the direct fill restorative to the tooth. Thermal stress may occur if the CTE of the direct fill restorative is not matched to the tooth. However, this theory has largely been dismissed by finite elemental analysis. These studies showed that the stress development is just a fraction of that developed by polymerization shrinkage.

Another strategy to prevent gap formation was to develop adhesives to maintain the bond integrity between the tooth and restoration. It was believed that if a strong bond between the tooth and restoration could be established, gap formation would be reduced, and secondary caries formation would also be reduced. In the mid-1950s, adhesion to tooth enamel was accomplished by using a technique where phosphoric acid etched the enamel. Using this technique resulted in a bond strength to enamel of about 20 MPa and was clinically stable. However, this technique alone did not prove to be effective in reducing secondary caries despite the bond strength. In addition to the bond strength with the enamel, adhesion to dentin and cementum was also thought to be necessary.

Improving adhesion to dentin and cementum continues to be a major focus. At least eight generations of adhesives have been developed. The first generation started in the mid-1950s where the adhesive contained a dentin coupling agent, glycerophosphoric acid dimethacrylate. The bond strength to dentin proved to be very erratic because of the hydrophobic resin matrix. Today, higher more consistent bond strengths have been achievable, in the 20-30 MPa range. However, despite being able to more consistently achieve high bond strengths, over time the bond strength deteriorates clinically. As a result, no clinical study using a dental adhesive has shown a reduction in the secondary caries rate.

Yet another approach to reducing secondary caries in direct fill composite resins has been to incorporate antimicrobials. This approach seems logical since there is a history of caries-resistant materials containing antimicrobials in dentistry. For example, zinc phosphate and zinc oxide eugenol cements, materials that contain zinc oxide, exhibit antimicrobial behavior and have good long-term caries resistance. Silver, which is a component in amalgam, also has antimicrobial activity.

Other antimicrobial compounds such as quaternary ammonium compounds and antibiotics have been incorporated into adhesives and direct fill composite resins. Examples of quaternary ammonium compounds include cetylpyridinium chloride (CPC). methacryloyloxdyododecylpyridinium (MDPB), poly-quaternary ammonium salts (PQAS) and methacryoxyethyl cetyl dimethyl ammonium chloride (DMAE-CB). Antibiotics such as ciprofloxacin, minocycline, cefaclor and metronidazone have been added directly to direct fill composite resins. These compounds have been incorporated into typical direct fill restorative formulations, but again there are no clinical studies that show a significant reduction in the secondary caries rate in composite resin restorations.

Despite the research to reduce gap formation and the introduction of antimicrobials into direct fill restorative formulations, the secondary caries in direct fill composite resin restorations continues to be a problem today. This is the main reason why the clinical life of these restorations has not improved. Other properties such as esthetics and clinical durability has made composite resins the choice of dentists for direct filling restorations. Yet, there is still a long felt need to extend the clinical life of these restorations. So, as a corollary, there exists a long felt need for a direct fill dental composite resin that reduces the incidence of secondary caries.

BRIEF DESCRIPTION OF THE INVENTION

This section discusses the concept of a direct fill dental restorative that contains a CTE that matches the tooth and an antimicrobial. The matched CTE minimizes the "Marginal Percolation" effect and allows long-term effectiveness of the antimicrobial. The net result is a caries resistant restoration that is effective whenever gaps are present. The concept requires the presence of both a CTE that matches the tooth and an antimicrobial.

A direct fill resin composite is a dental restoration material used in direct fill restoration procedures. Direct fill restoration procedures are restorations in which a dentist directly fills a cavity preparation. Specifically, a Class I-V lesion according to the G. V. Black classification of dental caries. The direct fill resin composite is placed, cured and finished in a single appointment. The major criteria for a direct fill restoration are that it is easily placed (typically a composite resin has viscosity and handling characteristics allowing it to be flowed into the cavity preparation), molded, sculptured, cured and finished in one appointment. Other criteria include excellent esthetics, mechanical properties and x-ray radiopacity. It should perform well clinically in both anterior and posterior restorations. Over the years, a host of materials including silicate cements, composite resins, glass ionomers, polycarboxylates and ionomer resins have been used as direct filling restorations. Overall, dentists feel that direct fill resin composites have met these criteria best and have become the material of choice in direct filling restorations.

An indirect restoration is a restoration that is fabricated outside the mouth usually by a dental laboratory. It is usually a more complex restoration such as a crown or bridge. An indirect restoration procedure involves multiple appointments and includes such steps as placing a temporary restoration, taking impressions, pouring models and making casts. When the restoration is completed, a dentist cements it into the cavity preparation and finishes it. Long periods may be involved before completing the restoration. Examples of indirect restorations include gold, metals and porcelains.

The key distinction between direct and indirect restoration procedures is where the restoration is finished. Because direct restoration procedures are finished in the oral cavity, materials that can polymerize, such as polymerizable composite resins, to fill the cavity preparation and bond the restoration to the patient's teeth are favored. Since indirect restorations procedures are finished outside the oral cavity and then placed into the cavity preparation, a wider group of materials can be used. For example, porcelains, ceramics and gold have a CTE that closely matches dentin. However, those materials require manipulation that cannot be done in an oral cavity. Specifically, ceramic and porcelains are materials that must be fired. The firing procedure involves subjecting the components that make up the ceramic and/or porcelain to extremely high temperatures such that the components melt and combine to form the ceramic or porcelain that is chemically distinct from components. The resulting ceramic or porcelain is then sculpted outside of the oral cavity into the final indirect restoration that is adhered to the patient's dentition. The firing procedure cannot be replicated in a patient's oral cavity because the equipment involved would not fit and the high temperature would cause catastrophic damage to the patient's health. The sculpting of the ceramic or porcelain requires an open space because the special tools necessary for the sculpting the material cannot fit into the patient's oral cavity. Because both direct and indirect restoration procedures have their own unique requirements, the materials involved will be unique to the procedure as well and are not interchangeable. In other words, a porcelain cannot be used in a direct fill restoration. Because this invention is for a direct fill restoration where the dentist needs to place, sculpture, cure and finish the restoration in one appointment, materials used for indirect restorations are not applicable.

Secondary caries occur when gaps exist between the tooth and restoration. There are several reasons why gaps occur. The previous discussion explains why gaps occur due to the properties of the restorative material and the adhesive itself. Operator error also causes gap formation. It has been reported that about 50% of all restorative failures are due to operator technique. When gaps occur, it is important that antimicrobial activity be present within the gaps to prevent bacterial growth and secondary caries. This invention protects against secondary caries in gaps between the tooth and restorative no matter how they occur.

Table 1 shows the CTE of some relevant materials in accordance to the international standard ASTM Method D696. The CTE of dentin is approximately in the range of 10-12 ppm/° C. So, the materials with the closest match would ideally be within that same range, most preferably as close to the CTE of dentin as possible. Note that the materials with matched or lower CTEs to the tooth have a history of low caries incidence, whereas amalgams and composites have high CTEs and a history of high secondary caries incidence. Note also that these materials do not use adhesives and have little or no bonding to the tooth. This suggests that except for retention, the adhesive bond may not be as important a factor in preventing secondary caries as previously believed.

TABLE 1

The Coefficient of Thermal Expansion (CTE) of various restorative materials

| Restorative Material | Coefficient of Thermal Expansion (CTE) ppm/° C. |
|---|---|
| Good Match | |
| Gold | 14 |
| Porcelain Fused Metal | 14 |
| Porcelain | 14 |
| Silicate Cement | 7.6 |
| Glass Ionomer Cement | 9 |
| Zinc Phosphate Cement | 4.6 |
| Poor Match | |
| Amalgam | 30 |
| Composite Resin | 35 |
| Zinc Oxide/Eugenol Cement | 35 |

However, a CTE that closely matches dentin alone does not necessarily result in a caries-resistant material. For example, porcelain has a CTE that closely matches dentin, but is not known for its caries resistance, mainly because it typically uses a composite resin as a cement. Note also that materials that have a higher CTE such as amalgams and composites (30-35 ppm/° C.) have a history of developing secondary caries. For these materials to work long-term clinically, it is often necessary to introduce a cement or liner. Gold, PFM and porcelain are materials used exclusively in indirect restoration procedures and cannot be used in direct restoration procedures.

There have been attempts to reduce the CTE of composite resins to prevent gap formation as previously discussed. As shown In Table 1, typical composite resins have a CTE of about 35 ppm/° C. In an attempt to reduce the CTE even further, various low CTE fillers have been used. Examples are quartz and fused silica which have a CTE of about $5 \times 10^{-7}$ ppm/° C. Even fillers with a negative CTE (expands as the temperature increases) have been tried. Yet, the CTE remains at about 35 ppm/° C. Thus, lowering the CTE of a composite resin is not a simple matter of just selecting the filler with the lowest possible CTE.

The reason for this is because the effect of fillers on the CTE of composite resins is not linear and the dentist requires a paste that can be molded and carved to reproduce tooth anatomy in a restoration. At low filler loading the resin matrix is not constrained and expands and contracts unhindered. In this situation, CTE of the composite resin remains that of the resin component. As the amount of filler particles is increased, the particles begin to interact and the CTE of the composite resin as a whole begins to be influenced by the particles. This interaction is maximized when the filler loading is the highest. Particle-to-particle interaction increases at an exponential rate and the composite takes on the physical properties of the filler.

However, as the amount of filler is increased, the consistency of the paste also increases and there is a limit to the amount of filler that can be added. If the amount of filler is too high, the paste becomes resin starved and mechanical properties begin to deteriorate. Further, the dentist needs to sculpt the paste to form tooth anatomy. If the paste is too highly filled, it becomes too stiff to be sculpted or to adapt the restoration to the cavity margins. Thus, the ability to maximize filler content to lower the CTE as much as possible is not a simple matter of just adding more filler.

There is a long history of failure of others to formulate a composite resin by simply selecting fillers with a low CTE. This is embodied by patents that have claimed to reduce the CTE of composite resins, but because of these limits the CTE of composite resins have been limited to about 35 ppm/° C. For example, Temin, S. (U.S. Pat. No. 4,188,317) has claimed a reduced CTE using a titanium silicate filler with essentially a 0 ppm/° C. CTE, but the reduction was only from 39.4 ppm/° C. for an amorphous silica filler to 30.4 ppm/° C. for titanium silicate. The reduced CTE value did not approximate that of dentin. So, clearly, just using a filler with a zero CTE by itself is not sufficient to lower the CTE of a composite resin to approximate dentin.

Table 2 lists dental restoratives that have a long history of being caries resistant. The materials listed all have two properties in common, they have CTE that closely matches that of dentin, 10-12 ppm/° C., and they have antimicrobial properties. The key is that they possess both of these properties. This combination has not been previously discussed in the literature.

TABLE 2

Restorative materials that have a history of caries resistance

Gold
Silicate cements

TABLE 2-continued

Restorative materials that have a history of caries resistance

Zinc phosphate cements
Polycarboxylate cements
Zinc oxide/eugenol cements
Calcium phosphate cements
Glass ionomer cements
Resin ionomers Note that composite resins are not on the list—they do not exhibit caries resistant properties. Some attempts have been made by the cements for use in direct filling restoration procedures, but these have failed mostly because of the other criteria needed, such as easy placement, esthetics, clinical durability, x-ray radiopacity, etc. . . .

Individually, a restoration that has a CTE that closely matches that of dentin alone or one that has antimicrobial properties alone does not necessarily produce a caries resistant material. For example, porcelains are not generally known as a caries resistant material but have a low CTE, 14 ppm/° C. Porcelains do not have antimicrobial properties. Amalgams contain silver, which has strong antimicrobial properties but is not a caries resistant material.

Why is it necessary to have both properties together in a caries resistant dental restoration? The key is a phenomenon described as "Marginal Percolation", which involves the CTE of the material and the tooth. When the CTE of the restoration is largely different than the tooth (for example composite resins and amalgams), any gap between the tooth and restoration expands and contracts at a different rate with temperature changes. The gap expands and contracts allowing bacteria and nutrients to percolate into the gap with temperature changes. This is what is described as "Marginal Percolation" which allows bacteria to thrive in the margins, resulting in secondary caries. On the other hand, if the CTE of the material and the tooth matches, any gap retains the same dimension, since the material and the tooth expands and contracts at the same rate with temperature changes. "Marginal Percolation" does not occur with these materials.

The "Marginal Percolation" effect was first discussed by Phillips (Phillips, R: The Science of Dental Materials; Saunders 1967). This discussion was on amalgam materials and was largely disputed because of the large temperature range of the experiment (0-60 deg. C.), which is not normally experienced in the mouth (the temperature range rarely goes beyond 37° C.). This discussion has been eliminated in subsequent editions of the book and the theory has been largely ignored since. However, this effect may be more important than previously thought.

If a gap exists between the material and the tooth, it is important that an antimicrobial exists within the gap to kill oral bacteria. Gaps occur between the material and the tooth no matter how good the restoration material or dental adhesive is. Most gaps form due to operator error. When this happens, it is important to have antimicrobial activity within the gap so that oral bacterial is killed. However, for long-term antimicrobial activity, it is important that "Marginal Percolation" within the gap does not occur. If this occurs, the antimicrobial is washed out of the gap with percolation and the antimicrobial is diluted. This is probably what happens with amalgam restorations.

The inclusion of an antimicrobial compound in the direct fill restorative will decrease the incidence of bacterial growth in gaps between the tooth and restorative at least initially.

The use of compounds that reduce the CTE of the material to closely match tooth dentin, will eliminate the "Marginal Percolation" effect, keeping the antimicrobial clinically effective in the long-term.

The combined features reduce secondary caries formation in gaps that occur between the tooth and direct filling restorative after placement by the dentist no matter what the cause.

DETAILED DESCRIPTION OF THE INVENTION

Some dental materials have performed well in terms of inhibiting secondary caries when used as a restorative. Gold restorations for example, have performed best, often lasting a lifetime clinically. Gold foil restorations adapt well and perform well without adhesives. Gold crowns also perform well with proven refractory cements. Probably the most important feature of gold as a dental material is its CTE.

Ideally, the CTE of dental materials should match the CTE of dentin or be substantially similar to the CTE of dentin. When this happens, the restorative and tooth expand and contract at the same rate as the temperature of the oral cavity cycles. This prevents stress from developing at the interface at the bond between the restorative and dentin and helps maintain an integral bond between the materials. More importantly, a matched CTE between the materials will prevent a phenomenon referred to as "Marginal Percolation". "Marginal Percolation" is a phenomenon whereby a gap expands and contracts in between the tooth and restorative. This gap changes dimensions because the dentin and restorative are expanding or contracting at different rates, allowing a continuous influx of bacteria and nutrients for established bacterial colonies into the gap. As discussed, there is a large difference in CTE between some dental restoratives and dentin (for example composites and amalgams have a CTE of about 30 ppm/° C. vs. 12 ppm/° C. for dentin). With temperature cycling, "Marginal Percolation" occurs and bacteria and nutrients percolate into the gap allowing bacterial growth. The existence of growing bacteria within the formed gap results in secondary caries. On the other hand, if the dentin and restorative are expanding and contracting at the same rate, this gap does not change in dimensions, resulting in less bacterial growth, and a corresponding decrease in secondary caries.

Operator error often results in marginal gaps between the tooth and restoration. Clinical studies have shown that more than 50% of restorative failures are a result of operator error. This is a matter of operator technique and happens no matter how good the restorative or adhesive is. In the situation where gaps occur and where there is a large difference in CTE between the tooth and restoration, "Marginal Percolation" occurs within the gaps. With temperature cycling, "Marginal Percolation" occurs and bacteria and nutrients percolate into the gap allowing bacterial growth.

Unfortunately, the importance of a matched CTE to the tooth has been marginalized in the past. The reason for this is that the difference is relatively small. All direct filling composites have a CTE of about 35 ppm/° C. vs. about 12 ppm/° C. for dentin (the high CTE is the result of the high CTE of polymers, about 80 ppm/° C.). The difference in CTE is small and probably has little effect on development of bond stresses compared to stress developed by polymerization shrinkage, which had been the focus of dental restorative research since the 1950s. As a result, the focus of past research has been to reduce polymerization shrinkage instead of matching the CTE.

Also reducing the CTE of composite resins has not been achieved due to the reliance on already existing materials used in dental restoratives. Most polymers used in dental restoratives have a CTE in the range of about 80 ppm/° C. Polymers with aromatic backbone such as BisGma have lower CTE of about 60 ppm/° C. Addition of inorganic fillers has reduced the CTE of composite resins to about 35 ppm/° C., However, further reductions in CTE to match the tooth has not been successfully explored in the current landscape of dental restorative materials. As a result, from a materials standpoint, there has been an absence of materials to formulate dental composite resins which are effective at being a restorative material and have a CTE which is within the range of dentin.

The present invention deals with a novel direct fill restorative that features resistance to the formation of secondary caries. Specifically, the primary feature of the direct fill composite resin disclosed below decreases the incidence of secondary caries by having a CTE that approximates dentin.

A filler was selected that would incorporate the low CTE feature of this invention as well as other properties necessary for a direct filling material. The CTE of the filler is less than 1 ppm/° C. The filler also produces other features necessary in a direct filling restoration, for example, excellent handling, sculptability, esthetics, mechanical properties, x-ray radiopacity and durability in anterior and posterior restorations, etc. . . .

As discussed above, simply selecting fillers with a low CTE is not sufficient to yield a composite resin with a CTE that approximates dentin. So, in addition to utilizing a filler with a low CTE, additional technology was introduced to improve particle-to-particle interaction while maintaining moldability and sculptability in the paste. A technique similar to the process of making steel was employed. In steel production, carbon particles are added to an iron matrix in a process called dispersion hardening. The result is the matrix is constrained and the composition is harder and stronger. The details of the ingredients and processing technology is a well-protected trade secret in the steel industry.

As discussed above, utilizing a particle size distribution that increases particle-to-particle interaction can increase the influence that the filler's CTE has on the composition as a whole. The high loading of the filler by itself is not sufficient to explain the low CTE value. Table 3 shows the CTE values and wt % filler loading of a typical hybrid composite, Nuance®, sold by Den-Mat Holdings, LLC, versus the low CTE direct fill restorative described by this invention as exemplified by Example 3 below. The CTE of the Nuance® is 36.9 ppm/° C., which is exemplary of composite resins; whereas the low CTE direct fill restorative is 12-15 ppm/° C., which is dramatically lower.

The low CTE value of the low CTE direct fill restorative cannot be explained simply by the increased filler loading in this case. Table 3 discloses the corresponding filler loading of both pastes. The wt % filler loading is similar for both pastes (78% vs. 79% by wt. correspondingly).

TABLE 3

| Material | Coefficient of Thermal Expansion ppm/° C. | Filler load wt % |
| --- | --- | --- |
| Nuance ® | 36.9 | 78 |
| Example 3 | 12.0-15.0 | 79 |

While it is true that higher filler loading with low CTE fillers may reduce the total CTE of a composite, other factors must also be considered. When the filler loading is very high, handling factors disclosed above apply. Further, higher loaded composite resins typically use larger filler particles in the range 25 microns or larger. The larger particles make it difficult to finish and polish by the dentist. And with wear, the composite surface becomes dull and rough to the tongue. For this reason, composite resins containing large particles are not favored. Highly filled composite resins with filler loading greater than 85% by wt. are disfavored for this reason and other handling issues disclosed above. Today, the composite resin market is dominated by nanofilled resins with smaller nanofillers that have more favored advantages.

In this invention, a trimodal distribution of filler particles is utilized to accomplish the low CTE values. The trimodal filler distribution allows for greater particle-to-particle interaction. It also allows filler particles to flow when a force is applied so that the paste may be molded and sculptured by the dentist. This results is an unexpectedly low CTE value of about 12-15 ppm/° C. in the cured paste, a match to the CTE of dentin.

The process involves a trimodal filler distribution. The trimodal filler distribution comprises of the following filler glasses: 15-50% by wt. submicron fillers, 0-15% by wt % 1 micron filler and 50-90% by wt % 5 micron fillers. This blend was uniformly dispersed and silanated with a coupling agent, for example, gamma methacryloxytrimethoxy silane, by jar milling.

When compounded into a paste, the interstitial space between the larger particles is filled with the medium sized particles, which allows greater particle-to-particle interaction. The smaller nanoparticle, (e.g. fumed silica), dispersion hardens the resin matrix further increasing particle-to-particle interaction. This contributes to the unexpectedly low CTE value.

Additionally, this novel dental restorative includes a compound with antimicrobial properties that are long lasting clinically. The activity does not have to be strong but must be long lasting. For example, zinc oxide has mild antimicrobial activity, but appears to be long lasting; whereas silver has strong activity but may not last as long. However, antimicrobial activity alone does not necessarily guarantee caries resistance. Amalgams, for example, contain silver and demonstrate good antimicrobial activity initially, but in the long term have proven to have a high rate of caries incidence. To be effective, caries-resistant materials must have antimicrobial activity throughout its restorative life.

Enduring antimicrobial activity may be related to the second important feature, ensuring that the dental restorative has a CTE that matches or is at least substantially similar to the CTE of dentin. As discussed, when this happens, the "Marginal Percolation" effect does not happen, and bacterial penetration and dilution of antimicrobials is minimized. The "Marginal Percolation" effect may help explain why some materials such as amalgams, lose their caries resistance over time. As illustrated in Table 1, silver in amalgams has strong antimicrobial activity, but amalgams also have a higher CTE value than the tooth. As a consequence, "Marginal Percolation" promotes dilution of the antimicrobial and also promotes bacterial penetration into the marginal gaps.

The invention also includes an antimicrobial to kill any bacteria present and would be effective should new gaps occur. As an antimicrobial compound, zinc oxide has several advantages. It has a long history of mild antimicrobial activity and long-term effectiveness.

Zinc oxide has been tested for antimicrobial activity in this invention according to a test that is based upon the International Standard AATCC TM 100-2012. The AATCC TM 100-2012 standard tests for microbial activity on textiles, so the test was modified for use on solid and composite materials. Under the modified AATCC TM 100-2012 test, zinc oxide has been found to be effective in killing bacteria.

Table 4 below demonstrates the effect of zinc oxide on the antimicrobial activity of a direct filling composite resin. As discussed above, microbial activity is measured using a modified AATCC TM 100-2012 standard for use on solid and composite materials.

TABLE 4

Effect of Zinc Oxide on *e. coli*

| Wt. Fract. ZnO | % Reduction of *e coli* | % reduction of strep mutans |
|---|---|---|
| 0 | 0% | 0% |
| 1.0% | 100% | 100% |

When zinc oxide is incorporated into a chemical for use in the oral cavity, it is typically incorporated for its function as an opacifying agent and can be added to a product for this function alone. However, there is a limit to the amount that can be added. Resins are esthetic restorative materials and require high translucency to be esthetic. For this reason, the amount of zinc oxide that may be added is limited to less than 0.8 wt. fract. See Table 5 for the upper limits of zinc oxide that can be incorporated into a direct fill composite resin while maintaining high translucency.

TABLE 5

Effect of Zinc Oxide on the translucency of a direct filling composite resin.

| Wt. Fract. ZnO | Translucency |
|---|---|
| 0 | pass |
| 0.8 | pass |
| 1.0 | fail |

In Table 5, as the wt. fraction of Zinc Oxide is increased, the opacity also increases to a level that is not considered suitable for use as a dental composite resin for esthetic purposes. For esthetic purposes, the dental composite resin must be sufficiently translucent to mimic the appearance of natural dentin. Beyond this level, the opacity becomes too high and the restoration appears as chalky white.

Dental restoratives used in core build up procedures are typically lower filled composite restoratives, used in internal portions of the teeth, where esthetics (color, translucency, surface finish) and wear properties are less important, and mechanical strength (>115 megapascals in flexural strength), microbial and CTE issues are of primary importance. Because of the decreased emphasis on esthetics for these types of dental restoratives, higher amounts, for example greater than 0.8%, of zinc oxide can be used. These materials are used to fill irregular, often small, undercut internal voids in the dentition, as well as being used to support implantable synthetic "core posts" (metal or fiber rods of 0.5-2 mm in diameter and 1-5 mm in length). Due to these variable uses, the viscosity of this class of materials is lower, not too dissimilar to that of an over the counter dentifrice.

This class of materials are often light cured, chemically "self" cured (via benzoyl peroxide curatives) as well as dual cured, allowing for light and self-cure with the same material. The material discussed here is dual cure, allowing for a fast cure via photo initiation, or allowing the material to cure more slowly on its own. When the composition is light cured, a photo initiator compound is included into the composition. A fairly typical photo initiator used in light cured dental composite restoratives is camphorquinine. However, any other suitable photo initiator can be used.

In order to prevent premature self-curing, this material is typically a two-component composition that are stored separately to allow the materials to maintain the desired viscosity (and not cure) and are admixed at the time of the dental procedure. The need for mixing as well as the aforementioned broad scope of use as a core material requires that the viscosity be relatively low, when compared to other conventional composite restoratives. Each component will contain compounds that are chemically inert by itself, however, when combined, will cure. In the embodiment discussed below in Table 6, component A contains benzoyl peroxide and component B contains dihydroxyethyl paratoluidine. When these chemicals are combined, the resulting chemical reaction will cure the resulting composition. Any other suitable binary curing system can be used instead of the combination of benzoyl peroxide and dihydroxyethyl paratoluidine.

In particular, this dental restorative is a material that is stored in a dual chamber syringe, and is dispensed through a static mixer tip, and is intended to be dispensed by hand pressure alone (no mechanical aids such as a cartridge dispensing gun, or other devices that provide mechanical advantage and reduce the force needed to dispense). As such, there is an implicit maximum to how thick the material can be, and still be practicably dispensed from the packaging by dental professionals, including those with below average hand strength.

Additionally, this dental restorative can also encompass the novel inclusion of bioactive components into the formulation. Bioactivity is determined in accordance with ISO/FDIS 23317. Such bioactive components allow for the formation of hydroxyapatite (the primary component of natural teeth) and allows the restoration to improve long term retention via the remineralized restoration surface "growing" into a single cohesive part of the tooth. As those skilled within the art are aware, the addition of bioactive materials imparts reduced mechanical properties of the final cured material.

The need for strong mechanical properties, as well as lower viscosity requirements, the bioactivity requirements, low CTE and antimicrobial components, provide a difficult set of desired properties that each can reduce the other properties.

An exemplary two-component direct fill dental restorative that incorporates zinc oxide and bioactive materials to yield a novel composite resin that exhibits antimicrobial materials and a CTE that is in the desired range to mimic dentin is as follows:

TABLE 6

Example 1: Dual Component low CTE Direct Fill Dental Restorative

| Chemical | Weight/weight percentage |
|---|---|
| Part A | |
| Hardener | 0.15-0.30 |
| diphenyl (2,4,6-trimehylbenzoyl) phosphine oxide | 0.07-0.09 |

TABLE 6-continued

Example 1: Dual Component low CTE Direct Fill Dental Restorative

| Chemical | Weight/weight percentage |
|---|---|
| Ethyl 4-dimethylaminobenzoate | 0.05-.15 |
| Camphorquinone | 0.05-0.15 |
| Resin Blend | 22-35 |
| 2-(2' hydroxy-5'-octylphenyl) benzotriazole | 0.4-0.5 |
| butylated hydroxytoluene | 0.008-0.01 |
| Trimodal Filler Glass Blend | 41-59 |
| fumed silica blend | 1.5 |
| Anti-Microbial | 0.2-0.75 |
| Calcium fluoride | 0-1.75 |
| Part B | |
| dihydroxyethyl paratoluidine | 0.6-0.9 |
| diphenyl (2,4,6-trimehylbenzoyl) phosphine oxide | 0.07-0.09 |
| Ethyl 4-dimethylaminobenzoate | 0.05-.15 |
| Photo Initiator | 0.05-0.15 |
| Resin Blend | 12-35 |
| 2-(2' hydroxy-5'-octylphenyl) benzotriazole | 0.4-0.5 |
| butylated hydroxytoluene | 0.008-0.01 |
| Trimodal Filler Glass Blend | 41-59 |
| fumed silica blend | 1.5 |
| Anti-Microbial | 0.2-0.75 |
| Calcium fluoride | 0-1.75 |
| Bioactive component | 9-12 |

An alternative embodiment would be a single component direct fill dental restorative that is light cured only (Table 7). Because this embodiment lacks the ability to self-cure the entire composition can be stored in a single component. However, lack of self-curing reduces the dental professional's flexibility in use.

TABLE 7

Single Component Low CTE Direct Fill Restoratives

| Chemical | Weight/weight % | |
|---|---|---|
| | Example 2 | Example 3 |
| diphenyl (2,4,6-trimehylbenzoyl) phosphine oxide | 0.07-0.09 | |
| Ethyl 4-dimethylaminobenzoate | 0.05-0.15 | 0.05-0.15 |
| Photo Initiator | 0.05-0.15 | 0.05-0.15 |
| Resin Blend | 32-90 | 20-35 |
| 2-(2' hydroxy-5'-octylphenyl) benzotriazole | 0.4-0.5 | 0.4-0.5 |
| Butylated hydroxytoluene | 0.008-0.01 | 0.008-0.01 |
| Trimodal Filler Glass blend | 50-71 | 75-85 |
| Fumed Silica blend | 1.5 | 0.5-1.5 |
| Anti-Microbial | 0.2-0.75 | 0.8-1.0 |
| Calcium fluoride | 0-1.75 | |

The method of manufacturing such a restorative is as follows:

1. Soluble components such as photoinitiators, inhibitors and stabilizers are dissolved into the resin.
2. The filler glasses and fumed silica (hydrophobic or hydrophilic or a blend of hydrophobic and hydrophilic) are pre-blended to create the trimodal filler distribution. The blend of filler glasses are silanated with a coupling agent.
3. The pre-blended filler glasses, fumed silica and zinc oxide are added to the resin in small increments until the desired viscosity of the dental restorative is achieved.
4. The ensuing composition is then placed in a roll mill.

Low CTE was achieved by employing a trimodal distribution of low CTE x-ray radiopaque filler at high loading. For example, using a filler with a CTE value of <1 ppm/° C. vs. a more typical x-ray radiopaque filler which as a CTE of about 4 ppm/° C. The lower CTE value allows further reduction of the CTE of the composite resin to about 15 ppm/° C., well within the range of dentin.

Zinc oxide is incorporated within the resin to provide enhanced antimicrobial activity. As illustrated by Tables 4 and 5, the amount of zinc oxide incorporated within the resin is sufficiently high enough to provide enhanced antimicrobial activity, but low enough to prevent opacity of the restorative.

The resin can be selected from the group of resins commonly used in direct fill dental restoratives. For example, some commonly used resins can include, but is not limited to, ethoxylated bisphenol A dimethacrylate, Bis GMA or triethylene glycol dimethacrylate. The resin can either be present individually, or as a blend of resins. Inhibitors and stabilizers may be added to the resin to extend the shelf life of the direct fill dental restorative.

The light curing direct filling composite restoratives disclosed in Tables 6 and 7 results in a restorative with excellent antimicrobial activity, mechanical properties and a CTE that closely approximates that of dentin (12-15 ppm/° C.). Moreover, the paste is very moldable and tooth anatomy may be sculptured into the restoration by the dentist. Antimicrobial activity follows the trend disclosed in Table 4.

The CTE achieved by a typical light curing direct filling composite, Nuance® (high viscosity Universal Composite restorative) by Den-Mat Holdings, LLC, as compared to the direct fill restorative described by Example 3 is shown in table 8. Nuance® was selected for the comparison because its properties are representative of the current state of the art of dental restoratives. The CTE was measured using the ASTM D 695 standard.

TABLE 8

Coefficient of thermal expansion (CTE) of direct filling composite resins

| Material | CTE ppm/° C. |
|---|---|
| Nuance ® | 36.9 |
| Example 3 | 16.1 |

Because, the caries-resistant direct filling composite must also function as a restorative material, its material characteristics must meet or exceed the current standards set by currently available dental restoratives. Table 9 compares the flexural strength between the Example 3, and Nuance®. The flexural strength was measured in accordance with the ISO 4049. As Table 9 indicates, the flexural strength of Example 3 exceeds that of Nuance®.

TABLE 9

| Material | Flexural Strength, Mpa |
|---|---|
| Nuance ® | 83.4 MPa |
| Example 3 | >113.0 MPa |

The foregoing description of the invention with the accompanying examples is not intended to be limiting. It is contemplated that other embodiments may be made without departing from the spirit or scope of the invention as set forth in the appended claims.

What is claimed is:

1. A direct fill composite restorative composition comprising:
    an antimicrobial agent;
    at least one resin;
    a photo initiator;
    a trimodal filler distribution with a filler load of at least or greater than 79%;
    wherein said trimodal filler distribution is comprised of 15-25% by w/w % submicron filler glass, 1-15% by w/w % 1 micron filler glass and 50-80% by w/w % 5 micron filler glass all having a coefficient of thermal expansion of less than 1 ppm/C; and
    whereas said trimodal filler distribution allows for greater particle-to-particle interaction and particle flow resulting in the coefficient of thermal expansion of said direct fill composite restorative composition to be in the range of 10-17 ppm/° C. and be used in direct fill dental restorative procedures to fill dental caries.

2. The direct fill composite restorative composition of claim 1 wherein said antimicrobial agent is comprised of zinc oxide.

3. The direct fill composite restorative composition of claim 2 wherein said zinc oxide is in the range of 0.2-0.8 w/w %.

4. The direct fill composite restorative composition of claim 1 further comprising a flexural strength greater than 83.4 MPa.

5. The direct fill composite restorative composition of claim 1 wherein said trimodal filler distribution is radiopaque.

6. The direct fill composite restorative composition of claim 1 wherein said at least one resin is selected from the group consisting of ethoxylated bisphenol A dimethacrylate, Bis GMA, triethylene glycol dimethacrylate and combinations thereof.

7. The direct fill composite restorative composition of claim 1 wherein said coefficient of thermal expansion is in the range of 10-15 ppm/deg C.

8. The direct fill composite restorative composition of claim 7 wherein said coefficient of thermal expansion is in the range of 14-17 ppm/deg C.

9. A dual component direct fill composite restorative composition comprising:
    a first component;
    said first component comprises of a first component of a binary curing system, a filler comprising of a trimodal filler distribution,
    said filler has a filler load at least or greater than 79%, at least one resin and an anti-microbial agent; and
    a second component;
    said second component comprises of a second component of a binary curing system, a filler comprising of a trimodal filler distribution, said filler has a filler load at least or greater than 79%, an anti-microbial, at least one resin;
    wherein said trimodal filler distribution is comprised of 15-25% by w/w % submicron filler glass, 1-15% by w/w % 1 micron filler glass and 50-80% by w/w % 5 micron filler glass all having a coefficient of thermal expansion of less than 1 ppm/C; and
    wherein both components are admixed prior to use to form said direct fill composite restorative composition with a coefficient of thermal expansion in the range of 10-17 ppm/° C. and used in direct fill dental restorative procedures to fill dental caries.

10. The direct fill composite restorative composition of claim 9 wherein said coefficient of thermal expansion is in the range of 10-15 ppm/deg C.

11. The direct fill composite restorative composition of claim 9 wherein said coefficient of thermal expansion is in the range of 14-17 ppm/deg C.

12. The direct fill composite restorative composition of claim 11 wherein said antimicrobial agent is comprised of zinc oxide.

13. The direct fill composite restorative composition of claim 12 wherein said zinc oxide is in the range of 0.2-0.8 w/w %.

14. The direct fill composite restorative composition of claim 9 wherein said first component of said binary curing system is comprised of benzoyl peroxide.

15. The direct fill composite restorative composition of claim 9 wherein said second component of said binary curing system is comprised of dihydroxyethyl paratoluidine.

16. The direct fill composite restorative composition of claim 9 wherein said at least one resin comprises ethoxylated bisphenol A dimethacrylate, Bis GMA, triethylene glycol dimethacrylate or combinations thereof.

17. A method of manufacturing a direct fill composite restorative composition comprising the steps of:

dissolving soluble components comprising of photoinitiators, inhibitors, and stabilizers into at least one resin;

blending together a trimodal filler distribution comprised of 15-25% by w/w % submicron filler glass, 1-15% by w/w % 1 micron filler glass and 50-80% by w/w % 5 micron filler glass all having a coefficient of thermal expansion of less than 1 ppm/° C. to form a trimodal distribution of filler glasses;

adding said trimodal distribution of filler glasses, fumed silica and at least one anti-microbial to said at least one resin to form said direct fill composite restorative composition;

and said direct fill composite restorative composition is placed in a roll mill;

wherein said direct fill composite restorative composition has a coefficient of thermal expansion in the range of 10-17 ppm/° C. for use in direct fill dental restorative procedures.

18. The method of claim 17 wherein said at least one anti-microbial comprises of zinc oxide.

19. The method of claim 18 wherein said zinc oxide is in the range of 0.2-0.8 w/w %.

\* \* \* \* \*